United States Patent
Edwards et al.

(10) Patent No.: US 7,510,732 B2
(45) Date of Patent: Mar. 31, 2009

(54) ANALGESIC AND ANTI-INFLAMMATORY COMPOSITION

(75) Inventors: Jeffrey D. Edwards, Claremont (AU); John Palermo, Leederville (AU)

(73) Assignee: Cambridge Scientific Pty Ltd, Leederville, WA (AU)

( * ) Notice: Subject to any disclaimer, the term of this patent is extended or adjusted under 35 U.S.C. 154(b) by 177 days.

(21) Appl. No.: 11/059,580

(22) Filed: Feb. 16, 2005

(65) Prior Publication Data

US 2006/0182811 A1    Aug. 17, 2006

(51) Int. Cl.
*A61K 35/16* (2006.01)
*A61K 38/48* (2006.01)

(52) U.S. Cl. ............... 424/530; 424/531; 424/94.64; 424/184.1; 424/400

(58) Field of Classification Search .......... 424/400, 424/184.1, 94.64, 530, 531

See application file for complete search history.

(56) References Cited

U.S. PATENT DOCUMENTS 5,888,522 A    3/1999    Pickart

FOREIGN PATENT DOCUMENTS

RU    2 221 456    1/2004

OTHER PUBLICATIONS

Chemical Abstracts online abstract and indexing of AN 141:220606 of RU 2 221 456, 2004 (accessed Jun. 17, 2008).
Chung et al., "Systemic and localized scleroderma", Clinics in Dermatology 24: 374-392 (2006).
Hume et al., "Eplcondylar Injury in Sport, Epidemiology, Type, Mechanisms, Assessment, Management and Prevention", Sports Medicine 36 (2): 151-170 (2006).
National Cancer Institute Dictionary of Cancer Terms, soft tissue definition, http://www.cancer.gov/Templates/db_alpha.aspx?CdrID=45882, accessed on Dec. 09, 2008.

*Primary Examiner*—Ruth A Davis
(74) *Attorney, Agent, or Firm*—Fish & Richardson P.C.

(57) ABSTRACT

The present invention discloses a composition that contains (1) an effective amount of an analgesically and/or anti-inflammatory active fraction separated from a mixture of plasma and/or serum, and (2) at least one metal, metal ion or metal salt, in which the mixture has been denatured. Also disclosed are methods of producing the composition for treating a subject afflicted with inflammation and/or pain.

19 Claims, No Drawings

000
ANALGESIC AND ANTI-INFLAMMATORY COMPOSITION

FIELD OF THE INVENTION

The present invention relates to an agent having analgesic and anti-inflammatory activity. In particular the present invention relates to a composition comprising an effective amount of an analgesically and anti-inflammatory active fraction separated from a mixture of plasma and/or serum and at least one metal, metal ion or metal salt thereof, wherein said mixture has been denatured.

BACKGROUND OF THE INVENTION

Pain can be defined as an unpleasant sensation ranging from mild discomfort to agonizing distress, associated with real or potential tissue damage, or a disorder of the nervous system. Pain is a response to impulses from the peripheral nerves in damaged tissue, which pass to nerves in the spinal cord. All animals experience some degree of pain during life, whether through injury or disease. As such, one of the major areas of drug research is the development of analgesics to be used in pain management.

One area in which pain is more frequently experienced than in others is inflammation. Pain associated with inflammation can be caused by pathologic processes in somatic structures or viscera or by prolonged dysfunction of parts the peripheral nervous system. Pain associated with inflammation may be the result of recurrent injuries, trauma, headache, arthritis including osteoarthritis, chronic obstructive pulmonary disease, psoriasis, or other pathologies. Pain associated with inflammation may be acute or chronic depending on the duration, level and extent of the inflammation.

Irrespective of the type or cause of pain it is important that early treatment is obtained as unrelieved pain can have profound psychological effects on the patient and acute pain which is poorly managed initially can degenerate into chronic pain which may prove more difficult to treat. However, the difficulty is that pain perception is a complex psychophysical process that can be modified by attitude, attention and suggestion. No other sensation depends as much on cognition and information processing as does pain. See, for example, Kling, J. W. and Riggs, L. A., Editors, Woodworth & Schlosberg's Experimental Psychology, 3rd. edition, Holt, Rinehart and Winston, Inc., New York, N.Y. (1971).

Therapeutic management of pain includes four steps:
1) peripheral level pain is treated with ice packs, heat pads, massage or non-steroidal anti-inflammatory drugs (NSAIDs) like aspirin or ibuprofen to inhibit local responses to trauma and prevent stimulation of nociceptors;
2) mild pain is treated with non-opioid analgesics such as paracetamol;
3) moderate or persisting pain is treated with a weak opioid like dihydrocodein plus non-opioid analgesics; and
4) severe pain that persists or increases is treated with a potent opioid eg nalbuphine plus non-opioid analgesic.

Despite all of the recent advances in the treatment of pain and/or inflammation, the majority of the agents used have side effects or limitations. For example, aspirin can cause irreversible inhibition of platelet function and cause gastric irritation. It can precipitate hypersensitivity reactions including asthma, and there may be cross sensitivity with other NSAIDs. It also interacts with a number of other drugs and is especially hazardous with warfarin.

Paracetamol does not have the haematological or GI adverse effects associated with aspirin and side effects are rare; however, overdosage is particularly dangerous as it may cause severe or sometimes fatal hepatic damage.

Mild NSAIDs such as ibuprofen have weaker anti-inflammatory properties than aspirin, but a much lower risk of GI side effects than aspirin and other NSAIDs.

Dihydrocodeine is a weak opioid which is effective for the relief of moderate pain of visceral origin. However, it is known to cause nausea, vomiting and constipation.

Co-dydramol and co-codamol are compound analgesic preparations which combine paracetamol with a low dose of an opioid analgesic eg. dihydrocodeine or codeine.

NSAIDs used regularly in full dosage have a lasting analgesic and anti-inflammatory effect which makes them particularly useful for treatment of continuous regular pain associated with inflammation, musculoskeletal and soft tissue disorders.

Diclofenac combines good efficacy with relatively low incidence of side effects. It is stronger than ibuprofen but has more side effects than ibuprofen. It is associated with intermediate risk of serious upper gastro-intestinal side effects.

As can be seen, many of currently used analgesics have associated side effects include dyspepsia, gastric or small bowel bleeding, ulceration, renal insufficiency, confusion, rash, headache, hepatic toxicity. NSAIDs also reversibly inhibit platelet aggregation and prolong bleeding time. Therefore, the use of analgesic compositions must be considered within the treatment context. At the same time, the treatment context is a factor that must be taken into account when considering the pharmacology and physiology of analgesic ingredients.

There is thus a continued need for new analgesics that can provide fast and reliable analgesia and preferably also anti-inflammatory benefits.

SUMMARY OF THE INVENTION

In a first aspect, the present invention provides a composition comprising an effective amount of an analgesically and/or anti-inflammatory active fraction separated from a mixture of plasma and/or serum and at least one metal, metal ion or metal salt thereof, wherein said mixture has been denatured.

The plasma or serum may be obtained from any animal source. Preferably, the plasma or serum is isolated from an animal selected from the group consisting of human, equine, bovine, ovine, murine, caprine and canine.

In one embodiment, the plasma and/or serum is dried and lyophilised before use.

Once the plasma and/or serum has been obtained it is mixed with at least one metal, metal ion or metal salt thereof. The metal, metal ion or metal salt thereof can be any metal. In one embodiment, the metal is selected from the group consisting of nickel, sodium, copper, zinc, cobalt, iron, magnesium, manganese, potassium, silver and mercury, ions or salts thereof and mixtures thereof.

Once the metal, metal ion or metal salt thereof has been mixed with the plasma and/or serum, it is preferably heated to at least 50° C. Preferably, the mixture is heated to about 65° C.

In one embodiment, a protease such as trypsin is preferably added before heating or after heating. At which point the resultant mixture is again heated then allowed to cool to produce an analgesic and/or anti-inflammatory mixture.

The second heating step is preferably carried out between about 80° C. and about 150° C., more preferably between about 90° C. and about 130° C. and most preferably, about 120° C. to produce said analgesic and/or anti-inflammatory mixture.

The analgesic and/or anti-inflammatory mixture can be used directly or further separated to produce an analgesically and/or anti-inflammatory fraction.

Preferably, the composition of present invention comprises at least a fraction of an analgesically and/or anti-inflammatory mixture as described above. More preferably, the composition of present invention is optionally admixed with a pharmaceutical carrier. Any pharmaceutical carrier known in the art may be used.

Accordingly, in a second aspect the present invention provides an analgesic and/or anti-inflammatory composition obtained by:
(a) heat denaturing a mixture of plasma and/or serum and at least one metal, metal ion or metal salt thereof; and
(b) separating an analgesically active and/or anti-inflammatory fraction from said denatured mixture.

Preferably, the step of separating the analgesically active and/or anti-inflammatory fraction is by chromatography such as affinity chromatography, column chromatography, partition chromatography, gel-filtration chromatography with a suitable solvent or solvent mixture.

In one embodiment, the method further comprises the steps of incubating said mixture in the presence of a protease to produce a digested mixture; and heating said digested mixture. These steps can be undertaken before or after addition of the at least one metal, metal ion or metal salt.

Accordingly, in a third aspect the present invention provides an analgesic and/or anti-inflammatory composition obtained by:
(a) heat denaturing a mixture of plasma and/or serum and at least one metal, metal ion or metal salt thereof;
(b) incubating said mixture in the presence of a protease to produce a digested mixture;
(c) heating said digested mixture; and
(d) separating an analgesically active and/or anti-inflammatory fraction from said denatured mixture.

Preferably, the step of separating the analgesically active and/or anti-inflammatory fraction is by chromatography such as affinity chromatography, column chromatography, partition chromatography, gel-filtration chromatography with a suitable solvent or solvent mixture.

In one embodiment, steps (b) and (c) are performed before the addition of at least one metal, metal ion or metal salt thereof. In a further embodiment step (a) further comprises the addition of $NaHCO_3$.

The step of denaturing the mixture by heat is preferably carried out at a temperature greater than 65° C.

The fractionation step (d) is preferably performed by chromatography on a polyamide column; however, any other method of fractionation may be used.

In a fourth aspect, the present invention provides a method for providing analgesia and reduction of inflammation to a subject, said method comprising administering to the subject an effective amount of a composition comprising an effective amount of an analgesically and/or anti-inflammatory active fraction separated from a mixture of plasma and/or serum and at least one metal, metal ion or metal salt thereof, wherein said mixture has been denatured.

The method of administration may be any method known in the art. Preferably, the composition is administered topically, systemically, intramuscularly, subcutaneously, intraperitoneally, intrapleurally, intraarticularly, intrathecally, rectally, vaginally, or by inhalation. Most preferably, the composition is administered topically.

In a fifth aspect, the present invention provides a composition for reducing inflammation and/or pain in a subject comprising a pharmaceutically acceptable carrier and an effective amount of an anti-inflammatory or analgesically active fraction separated from a mixture of plasma and/or serum and at least one metal, metal ion or metal salt thereof, wherein said mixture has been denatured.

In a sixth aspect, the present invention provides a physiologically active substance which is extracted from a mixture of plasma and/or serum and at least one metal, metal ion or metal salt thereof, wherein said mixture has been denatured.

Preferably, the physiologically active substance is further admixed with a pharmaceutically acceptable carrier. Preferably, the carrier is at least one member selected from the group consisting of distilled water, physiologically saline solution, Ringer's solution, plant oil, synthetic fatty acid glycerides, higher fatty acid esters, propylene glycol, lactose, mannitol, corn starch, crystalline cellulose, gum arabicum, gelatin, potato starch, carmerose, carmerose calcium, talc, and magnesium stearate.

In a seventh aspect, the present invention provides a method for treating a subject afflicted with inflammation and/or pain comprising administering an effective amount of an active fraction separated from a mixture of plasma and/or serum and at least one metal, metal ion or salt thereof, wherein said mixture has been denatured and wherein said fraction is admixed with a pharmaceutically acceptable carrier.

DETAILED DESCRIPTION OF THE INVENTION

Before describing the present invention in detail, it is to be understood that this invention is not limited to particularly exemplified methods and may, of course, vary. It is also to be understood that the terminology used herein is for the purpose of describing particular embodiments of the invention only, and is not intended to be limiting which will be limited only by the appended claims.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional chemistry and pharmacology within the skill of the art. Such techniques are well known to the skilled worker, and are explained fully in the literature. See, eg., Coligan, Dunn, Ploegh, Speicher and Wingfield "Current protocols in Protein Science" (1999) Volume I and II (John Wiley & Sons Inc.); The Merck Index, $12^{th}$ Edition (1996), Therapeutic Category and Biological Activity Index; and Remington's Pharmaceutical Sciences, $17^{th}$ Edition, Mack Publishing Company, Easton, Pa., USA.

It must be noted that as used herein and in the appended claims, the singular forms "a," "an," and "the" include plural reference unless the context clearly dictates otherwise. Thus, for example, a reference to "a metal" includes a plurality of such metals, and a reference to "an isolated protein" is a reference to one or more proteins, and so forth. Unless defined otherwise, all technical and scientific terms used herein have the same meanings as commonly understood by one of ordinary skill in the art to which this invention belongs. Although any materials and methods similar or equivalent to those described herein can be used to practice or test the present invention, the preferred materials and methods are now described.

In its broadest aspect, the present invention provides a composition useful as an analgesic and/or anti-inflammatory agent.

It will be appreciated that the term "anti-inflammatory" is intended to include an inflammatory response modifier, including all inflammatory responses such as production of stress proteins, white blood cell infiltration, fever, pain, swelling and so forth. Furthermore, the terms "analgesic," "analgesia," and "analgesically" as used herein interchangeably are intended to include a pain reliever that is capable of reducing pain sensation or nociception, whether the pain incurred is a result of disease, inflammation, trauma or psychosomatic reaction.

The composition of the present invention will therefore be administered as an effective amount to a subject in need of analgesia or anti-inflammatory treatment. The phrase "in need of analgesia" as applied to a subject herein embraces a subject suffering mild to intense pain at the time of administration of the composition of the present invention, as well as a subject that can reasonably be expected to have an imminent onset of mild to intense pain, eg., within about 1 to about 2 hours and especially within about 30 minutes, if no analgesic is administered.

The term "effective amount" refers to that amount which is sufficient to induce or maintain an analgesic effect or analgesia when administered to a subject; i.e., an analgesic-producing amount. Equally, the term "effective amount" when used with reference to the compositions anti-inflammatory activity means the amount sufficient to induce or maintain an anti-inflammatory effect. What constitutes an effective pain-relieving or inflammatory amount, or dose, of the composition of the present invention depends, among other factors, on the body weight of the subject and the intensity of the pain and/or inflammation being treated. Normally an effective dose will be found in the range of about 1 to about 6 mg/kg body weight. For an average 75 kg subject, this range equates to a dose of about 75 to about 450 mg. Proportionately smaller or larger doses can be appropriate for subjects having lesser or greater body weight. Such a dose can be administered as needed, but typically administration 1 to about 4 times per day, in most cases 1 or 2 times a day, provides adequate continuing relief of pain.

An "effective pain-relieving concentration" or "effective pain-relieving plasma concentration" as used herein is intended to mean a plasma level in a subject which when tested in a standardized test involving subject scoring of the severity of pain, achieves a mean score indicating pain relief. In one such test as described herein below, patients score pain on a scale of from 0 (no reduction in severity of pain) to 4 (complete relief of pain) and a mean score equal to or greater than a given value is deemed to constitute effective pain-relief. A mean score of 0.5 or greater and, more preferably, 1.0 or greater in such a test, as exemplified herein, is deemed to constitute effective pain relief. The skilled artisan will appreciate, however, that other approaches can be used to assess the severity of pain and relief from such pain.

Thus, one aspect of the present invention involves a therapeutic method for analgesia in which a composition comprising the composition of the present invention is administered to a subject, in a formulation which provides detectable pain relief. By "detectable pain relief", it is meant that the formulation produces effective pain relief which is measurable by a standard method such as described above. For example, a formulation, which achieves a mean score of 0.5 or greater and, more preferably, 1.0 or greater on a scale of from 0 to 4 in a testing system as described above, is deemed to provide detectable pain relief. The invention is not limited to use of any particular type of formulation, so long as it exhibits the pharmacokinetic profile defined herein. Examples of suitable formulation types are described below.

The composition of the present invention essentially comprises a mixture of plasma and/or serum and at least one metal, metal ion or metal salt.

The terms "plasma" and "serum" are used herein interchangeably; however, the term "plasma" typically refers to the straw-coloured fluid in which the blood cells are suspended. It consists of various inorganic salts of sodium, potassium, calcium etc. with a high concentration of protein (approximately 70 g/l) and a variety of trace elements. The term "serum" refers to the fluid that separates from clotted blood or blood plasma that is allowed to stand. Serum is essentially similar in composition to plasma, but generally lacks fibrinogen and others substances that are used in the coagulation process.

The plasma or serum used in the present invention may be obtained from any animal source. Preferably, the plasma and/or serum is isolated from blood taken from an animal selected from the group consisting of human, equine, bovine, ovine, murine, caprine and canine.

In one embodiment, the animal source for the plasma or serum is bovine.

The plasma or serum may be freshly isolated or alternatively lyophilised. In one embodiment, blood is isolated from cattle and the haemoglobin is removed by standard procedures. The plasma is then preferably mixed with sodium bicarbonate (approx. 20 g per liter) and heated to about 80° C. The coagulated plasma protein is then removed and lyophilised by standard procedures for further use.

In one embodiment the lyophilised plasma or serum is resuspended in water (approximately 50 g per liter) and mixed with at least one metal.

Various metals and/or metal ions are useful in the composition of the present invention and as such the present invention embraces all such metals or metal ions.

In one embodiment, the metals are selected from the group consisting of nickel, sodium, copper, zinc, cobalt, iron, magnesium, manganese, potassium, silver and mercury.

In cases where the metals are sufficiently basic or acidic to form stable non-toxic acid or base salts, the use of the metals as salts can be appropriate. Examples of acceptable metal salts include acetate, ascorbate, benzoate, bicarbonate, chloride, citrate, carbonate, $\alpha$-glycerophosphate, $\alpha$-ketoglutarate, malonate, methanesulfonate, nitrate, succinate, sulfate, tartarate and tosylate salts.

Metal salts can be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts can be made.

In one embodiment for example, the metal is silver (I), wherein the nitrate salt provides adequate free silver (I) ion to provide the necessary metal requirement. The chloride salt on the other hand provides less silver, being less soluble and with a low dissociation constant and therefore is less useful in the present invention. The skilled artisan will be able to readily determine the suitable salt form of the metal ion that provides the necessary properties for the present invention. Furthermore, the skilled artisan will be aware of the compatibility of the salt forms of the metal(s) and other components of the composition to maintain adequate levels of the metal ion(s).

In one embodiment, the metals used in the composition comprise a mixture of a number of metals. For example, the mixture of metals could consist essentially of $NiSO_4.7H_2O$, $NH_4VO_3$, $NaF$, $CuSO_4.5H_2O$, $ZnCl_2$, $(NH_4)_6MO_7O_{24}.4H_2O$, $COCl_2.6H_2O$, $FeSO_4.7H_2O$, $MgSO_4.7H_2O$, $H_3BO_3$, $MnCl_2.4H_2O$ and $K_2CrO_4$.

Once the metal, metal ion or metal salt thereof has been mixed with the plasma and/or serum, it is preferably heated to at least 50° C. Preferably, the mixture is heated to about 65° C.

In one embodiment, a protease selected from the group consisting of trypsin, chymotrypsin, factor Xa, venom-protease, thrombin, plasmin and a serine-protease of the subtilisin family is preferably added before heating or after heating. Preferably, the protease is trypsin.

The protease can indeed be added before the metal, metal ion or metal salt is added. Whichever, once the protease has been added the resulting mixture of plasma/serum and protease, with or without metal, metal ion or metal salt is incubated between about 30° C. and 45° C. for at least 30 minutes. The mixture is then heated again. The second heating step is preferably carried out between about 80° C. and about 150° C., more preferably between about 90° C. and about 130° C. and most preferably, about 120° C. to produce said analgesic and/or anti-inflammatory mixture.

Once the analgesic and/or anti-inflammatory mixture has been obtained it can be either used directly or fractionated to obtain an analgesically and/or anti-inflammatory active fraction. Techniques for fractionating protein-containing mixtures are well known in the art. See, for example, "Plasma Protein Fractionation" Heide K, Haupt H & Schwick H; in The Plasma Proteins, $2^{nd}$ Edition Vol 3 (1977) Putnam F. (Ed); U.S. Pat. No. 4,351,710 and U.S. Pat. No. 4,322,275 both entitled "Fractionation of protein mixtures"; U.S. Pat. No. 5,138,034 entitled "Method of fractionating plasma proteins" all incorporated herein by reference.

As described above, in one embodiment, the present invention provides a method of relieving pain and/or inflammation in a subject, the method comprising administering to the subject an effective pain- and/or inflammation-relieving amount of a composition of the present invention.

The method of the invention can be used to relieve mild to severe, acute or chronic pain. The method of the invention is useful for treatment of non-human mammalian subjects or patients, including domestic, farm and exotic animals, such as for example dogs horses, zoo animals and the like, but is primarily useful for treatment of human subjects or patients.

Generally, the terms "treating," "treatment" and the like are used herein to mean affecting an individual or subject, their tissue or cells to obtain a desired pharmacological and/or physiological effect. The effect may be prophylactic in terms of completely or partially preventing the pain or inflammation or sign or symptom thereof, and/or may be therapeutic in terms of a partial or complete cure of the pain or inflammation. "Treating" as used herein covers any treatment of, or prevention of pain or inflammation in a vertebrate, a mammal, particularly a human, and includes: (a) preventing the pain or inflammation from occurring in a subject that may be predisposed to the pain or inflammation, but has not yet occurred; (b) inhibiting the pain or inflammation, i.e., arresting its development; or (c) relieving or ameliorating the symptoms of the pain or inflammation, i.e., cause regression of the symptoms of the pain or inflammation.

While the methods of the present invention are primarily directed towards pain relief the compositions of the present invention are also useful in the treatment and/or prevention of a wide range of conditions and disorders mediated by COX-2, including but not restricted to disorders characterized by inflammation, pain and/or fever. Such compositions are especially useful as anti-inflammatory agents, such as in treatment of arthritis, with the additional benefit of having significantly less harmful side effects than compositions of conventional nonsteroidal anti-inflammatory drugs (NSAIDs) that lack selectivity for COX-2 over COX-1. In particular, such compositions have reduced potential for gastrointestinal toxicity and gastrointestinal irritation including upper gastrointestinal ulceration and bleeding, reduced potential for renal side effects such as reduction in renal function leading to fluid retention and exacerbation of hypertension, reduced effect on bleeding times including inhibition of platelet function, and possibly a lessened ability to induce asthma attacks in aspirin-sensitive asthmatic subjects, by comparison with compositions of conventional NSAIDs. Thus compositions useful in methods of the invention are particularly useful as an alternative to conventional NSAIDs where such NSAIDs are contraindicated, for example in patients with peptic ulcers, gastritis, regional enteritis, ulcerative colitis, diverticulitis or with a recurrent history of gastrointestinal lesions; gastrointestinal bleeding, coagulation disorders including anemia such as hypoprothrombinemia, hemophilia or other bleeding problems; kidney disease; or in patients prior to surgery or patients taking anticoagulants.

Such compositions are useful to treat a variety of arthritic disorders, including but not limited to rheumatoid arthritis, spondyloarthropathies, gouty arthritis, osteoarthritis, systemic lupus erythematosus and juvenile arthritis.

Such compositions are useful in treating inflammation in such diseases as migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury including brain edema, myocardial ischemia, and the like.

Such compositions are useful in treatment of pain, including but not limited to postoperative pain, dental pain, muscular pain, and pain resulting from cancer. For example, such compositions are useful for relief of pain, fever and inflammation in a variety of conditions including rheumatic fever, influenza and other viral infections including common cold, low back and neck pain, dysmenorrhea, headache, toothache, sprains and strains, myositis, neuralgia, synovitis, arthritis, including rheumatoid arthritis, degenerative joint diseases (osteoarthritis), gout and ankylosing spondylitis, bursitis, burns, and trauma following surgical and dental procedures.

Compositions of the present invention can also be used in combination therapies with opioids and other analgesics, including narcotic analgesics, Mu receptor antagonists, Kappa receptor antagonists, non-narcotic (i.e., non-addictive) analgesics, monoamine uptake inhibitors, adenosine regulating agents, cannabinoid derivatives, Substance P antagonists, neurokinin-1 receptor antagonists and sodium channel blockers, among others. Preferred combination therapies comprise a composition useful in methods of the invention with one or more compounds selected from aceclofenac, acemetacin, α-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis(acetylsalicylate), amfenac, aminochlorthenoxazin, 3-amino-4-hydroxybutyric acid, 2-amino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, α-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyaluminum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsalmide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen and zomepirac (see The Merck Index, 12$^{th}$ Edition (1996), Therapeutic Category and Biological Activity Index, lists therein headed "Analgesic", "Anti-inflammatory" and "Antipyretic").

Still other suitable formulations for use in the present invention can be found in Remington's Pharmaceutical Sciences, Mace Publishing Company, Philadelphia, Pa. 17$^{th}$ ed. (1985).

The terms "administration," "administering," and "administered" are used herein interchangeably. The analgesic and/or anti-inflammatory composition of the present invention may be administered orally including sublingual, topically, or parenterally in dosage unit formulations containing conventional non-toxic pharmaceutically acceptable carriers, adjuvants, and vehicles. The term "parenteral" as used herein includes subcutaneous injections, aerosol, intravenous, intramuscular, intrathecal, intracranial, injection or infusion techniques or rectal or vaginally. Preferably, the analgesic and/or anti-inflammatory composition of the present invention is administered together with a pharmaceutically acceptable carrier or diluent compatible with the composition. In preparing such composition, any conventional pharmaceutically acceptable carrier can be utilised.

The carrier material can be organic or inorganic inert carrier material suitable for oral administration. Suitable carriers include water, gelatin, gum arabic, lactose, starch, magnesium stearate, talc, vegetable oils, polyalkylene-glycols, petroleum jelly and the like. Furthermore, the pharmaceutically active preparations may contain other pharmaceutically active agents. Additionally, additives such as flavouring agents, preservatives, stabilisers, emulsifying agents, buffers and the like may be added in accordance with accepted practices of pharmaceutical compounding.

When the analgesic and/or anti-inflammatory composition of the present invention is administered orally, it is generally administered at regular intervals, conveniently at meal times or once daily. The analgesic and/or anti-inflammatory composition of the present invention can be made up in any conventional form including: (a) solid form for oral, rectal or vaginal administration such as tablets, capsules (e.g., hard or soft gelatine capsules), pills, sachets, powders, granules, and the like; and (b) preparations for topical administrations such as solutions, suspensions, ointments, creams, gels, micronised powders, sprays, aerosols and the like; (c) liquid formulations for intravenous administrated may also be prepared. Pharmaceutical preparations may be sterilised and/or may contain preservatives, stabilisers, wetting agents, emulsifiers, salts for varying the osmotic pressure and/or buffers.

For topical administration to the skin or mucous membrane the aforementioned analgesic and/or anti-inflammatory composition of the present invention is preferably prepared as an ointment, tincture, cream, gel, solution, lotion, spray; aerosol and dry powder for inhalation, suspension and the like. In fact, any conventional methods of preparing topical compositions can be utilised in this invention. Among the preferred methods of applying the analgesic and/or anti-inflammatory composition of the present invention is in the form of an ointment, gel, cream, lotion, spray; aerosol or dry powder for inhalation. A pharmaceutical preparation for topical administration to the skin can be prepared by mixing the analgesic and/or anti-inflammatory composition of the present invention with non-toxic, therapeutically inert, solid or liquid carriers customarily used in such preparation. These preparations generally contain 0.01 to 5.0 percent by weight, preferably 0.1 to 1.0 percent by weight, of the analgesic and/or anti-inflammatory composition of the present invention, based on the total weight of the peptide preparation.

In preparing the topical preparations described above, additives such as preservatives, thickeners, perfumes and the like conventional in the art of pharmaceutical compounding of topical preparation can be used. In addition, conventional antioxidants or mixtures of conventional antioxidants can be incorporated into the topical preparations containing the afore-mentioned active agent. Among the conventional antioxidants which can be utilised in these preparations are included N-methyl-α-tocopherolamine, tocopherols, butylated hydroxyanisole, butylated hydroxytoluene, ethoxyquin and the like. Cream-base pharmaceutical formulations containing the antigen preparation, used in accordance with this invention, are composed of aqueous emulsions containing a fatty acid alcohol, semi-solid petroleum hydrocarbon, ethylene glycol and an emulsifying agent.

Ointment formulations containing the analgesic and/or anti-inflammatory composition of the present invention comprise admixtures of a semi-solid petroleum hydrocarbon with a solvent dispersion of the analgesic and/or anti-inflammatory composition. Cream compositions containing the analgesic and/or anti-inflammatory composition of this invention preferably comprise emulsions formed from a water phase of a humectant, a viscosity stabiliser and water, an oil phase of a fatty acid alcohol, a semi-solid petroleum hydrocarbon and an emulsifying agent and a phase containing analgesic and/or anti-inflammatory composition dispersed in an aqueous stabiliser-buffer solution. Stabilisers may be added to the topical preparation. Any conventional stabiliser can be utilised in accordance with this invention. In the oil phase, fatty acid alcohol components function as a stabiliser. These fatty acid alcohol components function as a stabiliser. These fatty acid alcohol components are derived from the reduction of a long-chain saturated fatty acid containing at least 14 carbon atoms.

Formulations for aerosols are described in Drugs and Pharmaceutical Sciences, Marcel Dekker, New York, 72: 547-574 (1996). Furthermore, the analgesic and/or anti-inflammatory composition of the present invention can be delivered by dry powder inhalation. Such formulations and devices are described in Pharmaceutical Technology, June 1997, pp. 117-125.

Depending upon the mode or type of administration and the severity of the pain or inflammation, the treatment regime will vary. However, typically an individual is monitored hourly or daily, depending on the above factors, and the status of pain/inflammation is determined. Administration of the analgesic and/or anti-inflammatory composition of the present invention continue until the pain and/or inflammation is reduced or alleviated.

Protocols for conducting human pharmacokinetic studies are well known in the art and any standard protocol can be used to determine whether a particular composition of the present invention satisfies the pharmacokinetic criteria set out herein. An example of a suitable protocol is described below.

Throughout the specification, unless the context requires otherwise, the word "comprise" or variations such as "comprises" or "comprising", will be understood to imply the inclusion of a stated integer or group of integers but not the exclusion of any other integer or group of integers.

The invention will now be further described by way of reference only to the following non-limiting examples. It should be understood, however, that the examples following are illustrative only, and should not be taken in any way as a restriction on the generality of the invention described above. In particular, while the invention is described in detail in relation to the use of specific animal plasma and metals, it will be clearly understood that the findings herein are not limited to these ingredients.

EXAMPLE 1

Preparation of Analgesic and Anti-Inflammatory Composition 200 liters of sterile cattle blood was centrifuged at 1000-1300×g for 10 minutes and the haemoglobin was removed from the plasma. After centrifugation approximately 100 liters of plasma was gained, and transferred into a dish, suitable for heating and continuous mixing. To the plasma liquid 2 kg Sodium Bicarbonate ($NaHCO_3$) was added and mixed until the $NaHCO_3$ dissolved, then the solution was heated to 80° C. Denatured plasma protein was then recovered and placed on filter paper to dry. The solid sediment was then pressed to produce a 60 kg solid plasma-protein "block" which was then lyophilised by standard procedures. After this process the plasma-protein weighed approximately 8 kg and was used in the preparation of the analgesic/antiinflammatory preparation as described below.

A solution was then prepared comprising 152 liters of water, 8 kg dried plasma-protein as prepared above and 200 ml of a metal-containing solution. The constituents of the metal-containing solution are shown in Table 1.

TABLE 1

| METAL-CONTAINING SOLUTION | |
|---|---|
| $NiSO_4 7h_2O$ | 10.4 g/l |
| $NH_4VO_3$ | 1.2 g/l |
| NaF | 24.0 g/l |
| $CuSO_4 5H_2O$ | 20.0 g/l |
| $ZNCl_2$ | 47.0 g/l |
| $(NH_4)6MO_7O_{24} 4H_2O$ | 7.0 g/l |
| $COCl_2 6H_2O$ | 20.0 g/l |
| $FeSO_4 7H_2O$ | 100.0 g/l |
| $MgSO_4 7H_2O$ | 80.0 g/l |
| $H_3BO_3$ | 23.0 g/l |
| Glucose | 50.0 g/l |
| $MnCl_2 4H_2O$ | 36.4 g/l |
| $K_2CrO_4$ | 1.0 g/l |
| Glycine | 75.0 g/l |
| Citric Acid | 20.0 g/l |

Made up in a 200 ml solution with water, which was then stirred for at least 20 minutes.

The mixture was then heated up to 120° C. and maintained for two hours with constant mixing. During this time the plasma-protein dissolved and was sterilized. The resulting material was then held at a temperature of about 35° C. and 0.125 g/l of trypsin was added. The material was then allowed to incubate for approximately 2 hours. The digested material was then autoclaved and cooled to produce the analgesic/anti-inflammatory composition of the present invention.

EXAMPLE 2

Manufacture of a Topical Analgesic/Anti-Inflammatory Composition

A composition comprising the ingredients shown in Table 2 were mixed at 75-80° C. in a 250 liter vacuum homogenizer equipped with anchor and turbo mixers. Then the ingredients shown in Table 3 were added and the mixing was continued at 80-83° C. for 10 minutes with the aid of the turbo mixer.

A slow cooling process was then carried out using the anchor mixer. When the material reached 60° C., the vacuum was switched on until the end of the cooling.

At 40-45° C. the ingredients shown in Table 4 were added and mixed for 10 minutes. Mixing with the anchor mixer was continued until the mixture reached 25° C.

After a standing period of approximately 24 hours, the topical analgesic was ready for use.

TABLE 2

| Item No. | Amount Per Kg | Ingredients |
| --- | --- | --- |
| 1 | 20 g | Liposorb S20 (Tween 60) |
| 2 | 20 g | Cremaphor A6 |
| 3 | 10 g | Hydromyristenol |
| 4 | 40 g | Cetyl alcohol |
| 5 | 70 g | Corn Oil (Cold Pressed) |
| 6 | 30 g | Wheat Germ Oil |
| 7 | 0.24 g | Carrot Oil |
| 8 | 50 g | Isopropyl Myristate |
| 9 | 0.2 g | Butylated Hydroxytoluene B.P. |
| 10 | 3 g | Phenonip |

TABLE 3

| 11 | 400 g | Plasma protein from Example 1 |
| --- | --- | --- |
| 12 | 15 g | Propylene Glycol B.P. |
| 13 | 15 g | Hygroplex HHG |
| 14 | 2 g | Allantoin |
| 15 | 208 g | Purified Water B.P. |
| 16 | 10 g | Germaben II |
| 17 | 4 g | Veegum |
| 18 | 100 g | Purified Water B.P. |
| 19 | 0.04 ml | Potassium Bromide 50 g/l |
| 20 | 30.7 mg | Sodium Sulphide |
| 21 | 0.04 ml | Potassium Iodide 25 g/l |

TABLE 4

| 22 | 1.4 g | Chammomile Fragrence |
| --- | --- | --- |

Methodology

1) Add items 1 to 10 in a 250 liter steam pan and heat 75° C.;
2) Boil items 15 and 18 in the 150 liter pan and transfer 13 liters to the 50 liter pan and add Veegum and mix until homogeneous;
3) Add item 14 to the remainder of the Purified Water B.P. in the 150 liter steam pan at above 90° C. and mix. When dissolved add the items 12, 13 and 16 and maintain temperature at 75° C. with continual mixing;
4) Add the water phase (step 5) to the oil phase (step 3) and mix using a short shaft air mixer. Then add step 4 to this using a plastic sieve to ensure that no lumps are incorporated;
5) Add plasma protein from Example 1 and emulsify for 20 minutes, then continue stirring whilst water cooling to 40° C.;
6) Add items 19 to 21 allowing a few minutes in between each addition whilst mixing. Cool to below 30° C.

EXAMPLE 3

Clinical Trial on Topical Analgesic and Anti-Inflammatory Composition

Twenty-three (23) randomly selected patients in a general practice setting were supplied with a preparation produced according to Example 2 above. The patients we advised to apply the preparation topically three times daily.

Patients were reviewed at regular intervals and divided into two groups:

Group A—work or injury induced conditions either acute or sub-acute eg repetitive strain injury (RSI), tennis elbow, joint and musculo-tendinous injury;

Group B—Arthritic and aging conditions—sub-acute and chronic eg osteoarthritis.

Table 5 shows the effect of using the topical composition over a three (3) month period.

TABLE 5

| Patient Details | Complaint | Result | Comments |
| --- | --- | --- | --- |
| Male - Aged 52 | Lateral epicondylitis | Improved | Full recovery |
| Male - Aged 28 | Musculo-tendinous | Full recovery | Acute soft tissue injury |
| Female - Aged 33 | Cervical soft tissue injury | Improved | Recovery after 1 week |
| Female - Aged 38 | RSI | Partial improvement | Rapid improvement, but relapse after cessation of treatment |
| Female - Aged 41 | RSI | No benefit | Poor patient selection - no treatment has worked |
| Female - Aged 64 | Reputed disc | No benefit | Pathology not treatable using analgesics/anti-inflammatory agents |
| Male - Aged 30 | Soft tissue injury | Improved | Soft tissue injury |
| Female - Aged 36 | RSI | No benefit | Too greater area to be treated with a topical agent |
| Female - Aged 50 | Lateral epicondylitis | Improved | Non-repetitive injury - Unsuccessfully treated with physiotherapy/anti-inflammatory agent |
| Female - Aged 68 | Arthritis | Improved | Pain relief but movement still restricted |
| Male - Aged 47 | Soft tissue injury | Improved | Rapid improvement, but relapse after cessation of treatment |
| Female - Aged 48 | Cervical soft tissue injury | Partial improvement | Poor compliance |
| Male - Aged 60 | Arthritis | Improved | Rapid improvement, but relapse after cessation of treatment. Intra-articular cortisone not effective |
| Female - Aged 70 | Arthritis | Improved | Rapid pain relief obtained |
| Male - Aged 68 | Arthritis | Improved | Rapid improvement, but relapse after cessation of treatment. |
| Female - Aged 56 | Arthritis | Improved | Pain relief obtained |
| Female - Aged 49 | Gout | Improved | Pain relief obtained |
| Female - Aged 80 | Calcaneal spur | No benefit | Condition not treatable with topical agent |
| Female - Aged 79 | Arthritis | Pain relief | Pain relief obtained |
| Female - Aged 69 | Arthritis | No benefit | Non-specific arthritis |
| Male - Aged 73 | Arthritis | No benefit | Poor patient selection |
| Male - Aged 67 | Inflammation | No benefit | Topical application not effective for this rheumatoid arthritis-like condition |
| Female - Aged 63 | Arthritis | No benefit | Multiple pathologies |

While these data are more qualitative than quantitative, it is readily apparent that use of the topical analgesic composition produced effect.

It was observed that in the more chronic situation, elderly, local arthritis (in particular osteo-arthritis), results were more predictable. Clinically, it appears that local application of the topical analgesic agent to a pathological joint produces some effect. This may in some way be related to the "massage" effect, and focusing attention of the positive aspects of treatment.

One of the most important aspects of the trial was selection of patient. Inventors believe that the nature of condition to be treated has an affect on the ability of a topical agent to work effectively. Of the small numbers used in this trial, the best results were obtained with patients having single joint pain or relatively localized non-joint pain. Patients whose general health was reasonable was more important than the age of patient. Finally, non-weight bearing joints responded more quickly than weight bearing joints.

Of the patients in Group A (acute and sub-acute), the best results were obtained where local rather than vague general pain was evident. Repetitive strain injury was not helped by the use of the analgesic unless the condition was of the very local category—eg. Tennis elbow. Conversely, with the "arthritic" Group B pain from osteo-arthritis was definitely reduced whilst the analgesic was being used. However, following cessation of treatment in may instance, the pain gradually returned.

EXAMPLE 4

Treatment of Osteoarthritis in Randomized Double Blind Study

Without wishing to be bound by any particular hypothesis or theory, the inventors believe that the active agents within the compositions of the present invention are metallo-peptide complexes. When used topically this preparation has been shown to be as effective as orally administered indocid (Indomethacin), a NSAID which reduces pain, swelling, and inflammation or phenylbutazone, a NSAID used in the treatment of pain, lameness, laminitis and osteoarthritis, in an animal model of inflammatory arthritis. The animal model was inflammation caused by an injection of mycobacteria into the foot pads of Long-Evans rats (data not shown).

In has also been demonstrated that the composition described in Example 2 possessed inhibitory activity against the serine proteinases-trypsin and human granulocyte elastase (HGE). Since HGE has been implicated in the destruction of cartilage in inflammatory arthritis the inhibitory properties of the composition in Example 2 against this or similar enzymes may contribute to its overall biological activity. Apart from these direct effects it is postulated that the compositions of the present invention might also work indirectly by acting as an agent for specific transdermal transport essential metals into the affected joints.

In order to test some of these theories patients aged 18 or over were treated three times daily with either the composition described in Example 2 or a placebo. Neither the patient nor the physician was aware of which agent they received. All patients were assessed to have mild to moderate non-advanced osteoarthritis of hand joints or knee joints will be entered. The patients were assessed before using the composition and two weeks after commencement of treatment. Joint pain was assessed both via palpation, movement and scored by the following scale:

0—Not Tender; 1—Tender; 2—Tender & Winced; 3—Tender, Winced & Withdrew.

Pain, morning stiffness and function were also subjectively assessed by the patient using the 10 cm visual analogue scale.

At the end of the two weeks the patients were asked to assess the composition as to its efficacy, scoring a percentage between 0-100%.

Twenty-two patients completed the trial—three males and nineteen females. The average age was 60, and the distribution of placebo and composition was approximately equal throughout the age range. The degree of severity and joints involved were also similar for the placebo and composition groups. Thirteen patients used the composition from Example 2 and nine used the placebo. The results are shown in Table 6.

TABLE 6

| | Treatment Group | |
|---|---|---|
| | Before Treatment (Mean ± SD) | After Treatment (Mean ± SD) |
| Palpation | 2.53 (0.96) | 0.38 (0.86)* |
| Movement | 1.70 (0.85) | 0.30 (0.85)* |
| Visual Analogue | | |
| Pain | 56.5 (16.8) | 23.4 (22.0)* |
| Morning Stiffness | | |
| Mins | 23.46 (25.85) | 11.69 (22.12) NS |
| Degree | 47.30 (30.83) | 10.76 (27.98) # |
| Function | 55.38 (20.79) | 25.38 (16.98)* |
| Patient Overall Assessment | | 75% |
| | Placebo Group | |
| | Before Treatment (Mean ± SD) | After Treatment (Mean ± SD) |
| Palpation | 2.66 (0.70) | 1.88 (0.95) NS |
| Movement | 2.22 (0.83) | 1.66 (0.95) NS |
| Visual Analogue | | |
| Pain | 54.44 (13.09) | 38.33 (27.27) NS |
| Morning Stiffness | | |
| Mins | 44.44 (57.46) | 17.0 (40.92) NS |
| Degree | 29.44 (30.82) | 19.4 (25.98) NS |
| Function | 66.6 (22.51) | 50.5 (33.35) NS |
| Patient Overall Assessment | | 45% |

Statistical Significance
*$P < .01$
$P < .1$
NS Not Significant

This double-blind trial was carried out on patients with clinically well defined osteoarthritis, both placebo and drug treated groups having a similar degree of severity, average age and similar spread of joint involvement. Although the number of patients was not large there was a clear difference between the drug treated and the placebo groups (see Table 6). These differences were shown to be statistically significant to the $P<0.01$.

The pain score both on palpation and movement was significantly reduced after two weeks of treatment with composition. All measures via the visual analogue scale were also significantly reduced. In contrast none of the parameters measured with the placebo group showed a significant reduction.

When asked to assess the efficacy of the treatment composition, the treated group scored a 75% approval for product, while the placebo group only had a 45% approval rate.

As the only difference between the two compositions was the plasma protein from Example 1, it must be assumed that this product was responsible for the therapeutic effects observed.

EXAMPLE 5

Topical Treatment in Non-Human Animals

Arthritis is a very common problem in certain dog breeds such as Rottweilers with clinical signs usually becoming evident at about 4-6 months of age.

This trial was therefore conducted on a "double blind" basis to ascertain whether or not the composition described in Example 2 was capable of reliving symptoms. Twenty-seven dogs were admitted into the trial, twenty-six Rottweilers (including one crossbred Rottweiler) and a Labrador. There was a fairly even distribution of immature and mature dogs and both acute and chronic conditions being treated. A brief summary of the individual results is given in Table 7. The placebo was designated A, while the active agent was designated B.

TABLE 7

| No | BREED | TREATMENT | RESULTS |
|---|---|---|---|
| 1 | Rottweiler | B only | No response and withdrew |
| 2 | Rottweiler | B only | Possible skin reaction to cream and withdrew |
| 3 | Rottweiler | B then A | Some improvement with B, no change with A |
| 4 | Rottweiler | A then B | Improved with A, then worse with B |
| 5 | Rottweiler | A then B | No response to either |
| 6 | Rottweiler | A then B | No response to either |
| 7 | Rottweiler | B only | Lost to follow up |
| 8 | Rottweiler | A then B | No response to either |
| 9 | Rottweiler | B then A | Improved on B, then worse with A |
| 10 | Labrador | B then A | Marked improvement on B, sustained while on A. (NB: older dog with chronic arthritis and both elbows treated) |
| 11 | Rottweiler | A only | No change on A, (both legs) then lost to follow up |
| 12 | Rottweiler | B then A | Improved on B then further on A |
| 13 | Rottweiler | A only | Euthanized after 1 week due to severe hip dysplasia. (Both legs treated) |
| 14 | Rottweiler | B then A | Minimal improvement on B, then further improved on A (Both legs treated) |
| 15 | Rottweiler | A then B | No change with A, slight improvement with but dog was rested |
| 16 | Rottweiler | B then A | Improvement on B, then slipped back again on A. (older dog with chronic arthritis, post surgery) |
| 17 | Rottweiler | B only | Improved in 2-3 days (old post surgery case) Not given A |
| 18 | Rottweiler | B then A | Improved to soundness in 2 days on B. Sesamoid problem developed while on A which did not respond to B treatment. |
| 19 | Rottweiler | B then A | Intermittent lameness improved to soundness on B, and this sustained while on A and for at least 3 months |
| 20 | Rottweiler | A then B | No response, worse on B than A |
| 21 | Rottweiler | B only | Chronic problem in elbows, complicated by sesamoid fragmentation during treatment. B used on L elbow and R sesamoid and dog became sound and has remained so. |
| 22 | Rottweiler | B then A | No response. Very severe case, both legs treated. Dog was destroyed. |

TABLE 7-continued

| No | BREED | TREATMENT | RESULTS |
|---|---|---|---|
| 23 | Rottweiler | A then B | No response. |
| 24 | Rottweiler | A then B | Slight improvement on A, but then lameness shifted to other leg. No further change on B. |
| 25 | Rottweiler | B then A X | No response. (Chronic post surgery case which was sound until slipped on stairs 4 weeks before entering trial) |
| 26 | Rottweiler | A then B | No change on A - results with B to come |
| 27 | Rottweiler | A then B | Results to come |

The most simple way to examine these results is to assess them on the basis of the "first used" treatment. When this is done, the results are as follows:

| | TUBE A | TUBE B |
|---|---|---|
| No. of dogs treated | 11 | 15 |
| No of dropouts | 2 | 2 |
| No. completing trial | 9 | 13 |
| No. responding (less lame) | 2 | 10 |
| % RESPONDING | 22.2 | 76.9 |

These results are at first glance better than we expected when we surveyed the combined results of the double-blind study. However, the 77% response rate must be interpreted in the light of a 22% response rate to the placebo (Tube A). Both these results may have been influenced by the weather patterns brought about by running this trial in the Spring. A number of the dog owners suggested that warmer weather at the time of treatment may have been at least in part responsible for the improvement in their dog's lameness. This comment is particularly applicable to Dog 14, which was recorded as a positive response but improved further on Tube A after finishing 2 weeks on Tube B.

What is claimed is:

1. A method of producing an analgesic composition comprising:
   (a) providing serum, plasma or a mixture thereof;
   (b) combining the serum, plasma or mixture thereof with a metal or metal ion solution; and
   (c) heating the serum or plasma or a mixture thereof to produce a mixture containing denatured proteins; and
   (d) collecting the denatured proteins as an analgesically active fraction.

2. A method according to claim 1, further comprising fractionating the denatured proteins by chromatography wherein the chromatography is affinity chromatography, column chromatography, partition chromatography, or gel-filtration chromatography with a suitable solvent or solvent mixture.

3. A method according to claim 1, further comprising the steps of incubating the collected denatured proteins in the presence of a protease to produce a digested mixture; and heating the digested mixture.

4. A method according to claim 1, wherein the plasma and/or serum is dried and lyophilised before use.

5. A method according to claim 1, wherein the metal is selected from the group consisting of nickel, sodium, copper, zinc, cobalt, iron, magnesium, manganese, potassium, silver and mercury, ions or salts thereof and mixtures thereof.

6. A method according to claim 1, wherein the metal is a mixture of metals consisting essentially of nickel sulphate heptahydrate ($NiSO_4.7H_2O$), ammonium vanadate ($NH_4VO_3$), sodium fluoride (NaF), copper (II) sulphate pentahydrate ($CuSO_4.5H_2O$), zinc chloride ($ZnCl_2$), hexaammonium heptamolybdate tetrahydrate (($NH_4)_6MO_7O_{24}.4H_2O$), cobalt (II) chloride hexahydrate ($COCl_2.6H_2O$), iron(II) sulfate heptahydrate ($FeSO_4.7H_2O$), magnesium sulphate heptahydrate ($MgSO_4.7H_2O$), boric acid ($H_3BO_3$), manganese dichloride tetrahydrate ($MnCl_2.4H_2O$) and potassium chromate ($K_2CrO_4$).

7. A method according to claim 1, wherein the heating step is at a temperature of at least 50° C.

8. A method according to claim 1, wherein the heating step is at a temperature of about 65° C.

9. A method according to claim 1, wherein a protease added before heating or after heating.

10. A method according to claim 9, wherein the protease is selected from the group consisting of trypsin, chymotrypsin, factor Xa, venom-protease, thrombin, plasmin and a serine-protease of the subtilisin family.

11. A method according to claim 9, wherein the protease is trypsin.

12. A method according to claim 9, wherein the mixture is further heated after addition of trypsin.

13. A method according to claim 12, wherein the further heating step is at a temperature between about 80° C. and about 150° C.

14. A method according to claim 12, wherein the further heating step is at a temperature between about 90° C. and about 130° C.

15. A method according to claim 12, wherein the further heating step is at a temperature about 120° C.

16. An analgesic composition produced according to claim 1.

17. A composition according to claim 16, further admixed with a pharmaceutical carrier.

18. A composition according to claim 17, wherein the pharmaceutical carrier is at least one member selected from the group consisting of distilled water, physiologically saline solution, Ringer's solution, plant oil, synthetic fatty acid glycerides, higher fatty acid esters, propylene glycol, lactose, mannitol, corn starch, crystalline cellulose, gum arabicum, gelatin, potato starch, carmerose, carmerose calcium, talc, and magnesium stearate.

19. The method of claim 1, further comprising incubating the serum, plasma or mixture thereof in the presence of a protease to produce a digested mixture, wherein the incubating is performed before or after the combining step.

* * * * *

UNITED STATES PATENT AND TRADEMARK OFFICE
CERTIFICATE OF CORRECTION

| | | |
|---|---|---|
| PATENT NO. | : 7,510,732 B2 | Page 1 of 1 |
| APPLICATION NO. | : 11/059580 | |
| DATED | : March 31, 2009 | |
| INVENTOR(S) | : Jeffrey D. Edwards et al. | |

It is certified that error appears in the above-identified patent and that said Letters Patent is hereby corrected as shown below:

On the Title Page,

[*] Notice: Subject to any disclaimer, the term of this patent is extended or adjusted under 35 USC 154(b) by 177 days.

Delete the phrase "by 177 days" and insert -- by 169 days --.

Title Page, Item (56) (Other Publications), Col. 2, Line 5, delete "Eplcondylar" and insert -- Epicondylar --.

Col. 19, Line 3, Claim 6, "($CuSO_4.5H_2O$)," and insert -- ($CuSO_4.5H_2O$), --.

Col. 19, Line 4, Claim 6, "($(NH_4)_6MO_7O_{24}.4H_2O$)," and insert -- ($(NH_4)_6Mo_7O_{24}.4H_2O$), --.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,510,732 B2 | Page 1 of 1 |
| APPLICATION NO. | : 11/059580 | |
| DATED | : March 31, 2009 | |
| INVENTOR(S) | : Edwards et al. | |

It is certified that error appears in the above-identified patent and that said Letters Patent is hereby corrected as shown below:

On the Title page,

[*] Notice:  Subject to any disclaimer, the term of this patent is extended or adjusted under 35 U.S.C. 154(b) by 177 days.

Delete the phrase "by 177 days" and insert -- by 355 days --

Signed and Sealed this

Twenty-second Day of June, 2010

David J. Kappos
*Director of the United States Patent and Trademark Office*